United States Patent [19]

Abbott

[11] 4,176,453

[45] Dec. 4, 1979

[54] DENTAL DRILL

[76] Inventor: Sheldon J. Abbott, 1068 Hicksville Rd., Massapequa, N.Y. 11758

[21] Appl. No.: 722,554

[22] Filed: Sep. 13, 1976

[51] Int. Cl.² ............................................. A61C 1/08
[52] U.S. Cl. ...................................... 433/82; 433/91
[58] Field of Search .......................... 32/33, 28, 27, 26

[56] References Cited

U.S. PATENT DOCUMENTS

| 751,261 | 2/1904 | Clarke | 32/23 |
|---|---|---|---|
| 3,092,908 | 6/1963 | Flatland | 32/27 |
| 3,525,154 | 8/1970 | Lieb | 32/28 |

Primary Examiner—Robert Peshock
Attorney, Agent, or Firm—Richard L. Miller

[57] ABSTRACT

This invention relates to a dental drill which includes a built in fluid conveying tube to supply a fluid in the form of water which becomes a mist when it strikes a rotating burr. The drill also includes a built in suction apparatus which can aspirate fluid and air from the area around the burr during the course of the drilling operation. The burr is usually driven by means of an air turbine, but the aspirated fluid-air mixture can be made to pass transversely across the turbine becoming the driving force for rotating the burr.

2 Claims, 4 Drawing Figures

DENTAL DRILL

BACKGROUND OF THE INVENTION

This invention relates to dental drills and more particularly to a drill capable of supplying water and aspirating fluid and air.

In carrying out dental drilling operations, it is often necessary to provide a fluid in the area being drilled to wash away the debris and keep the area free and clean from blood, or other contaminants. As a result, water is often sprayed simultaneously with the drilling operation. Such spraying is frequently provided by a separate water conveying tube from a separate fluid delivering surgical instrument. Sometimes, it is connected to the drill itself to thereby remove the need for a separate surgical instrument to provide the water. The water is typically discharged adjacent to the rotating burr so that as it strikes the burr it is formed into a mist which sprays onto the drilling area.

An additional problem, however, results from using the water to clean the drilling area. While the fluid in the form of the water does remove the debris and contaminant from the area being drilled, the detrimental effects of the water which is dispersed into the mist by means of the rotating burr, in many cases overpowers the beneficial results desired. For example, after the water strikes the rotating burr and forms into a mist, the mist can fog up the mirror or other instrument being used by the dentist or technician and requires frequent cleaning of those instruments during the course of the drilling operation. Additionally, the water must be removed from the mouth of the patient. Usually, water is removed by means of hanging a fluid aspirator into the patient's mouth. However, this merely provides low volume aspiration. The major portion of the fluid is generally removed by means of a high speed suction which is hand held by an assistant. However, the mist has a tendency of jumping in all directions including the exterior of the mouth and therefore the mist can be aspirated by the dentist and the assistant. Additionally, the patient himself may aspirate some of the water in the form of the mist which will cause additional problems to the patient.

A further problem exists with standard drilling assemblies. The burr is usually driven by means of an air turbine which requires a flow of air to be supplied to the turbine head under pressure to drive the turbine thereby rotating the burr. The air then escapes from the drill head assembly after turning the turbine. The escape of such air creates a high pitched whine which is most annoying to the patient.

Thus, the standard dental drilling apparatus is noisy, produces a mist which can be aspirated by the dentist, assistant and patient, and requires the need of additional personnel to aspirate the fluid and air in the area of the drilling operation.

SUMMARY OF THE INVENTION

It is therefore an object of the present invention to provide a dental drill which avoids the aforementioned problems of prior art devices.

Still another object of the present invention is to provide a dental drill which includes fluid delivering apparatus which provides water which can strike the rotating burr and disperse into a mist in the vicinity of the drilling area, and fluid removing apparatus for aspirating the fluid and air from the drilling area.

Yet another object of the present invention is to provide a dental drill which includes a built in fluid aspirator for removing fluid and air from the dental area being drilled, and utilizes the aspirated fluid and air to aid in driving the drill burr.

A further object of the present invention is to provide a dental drill having a turbine for driving a burr and which includes an aspirator for removing fluid from the area being drilled and utilizes the removed fluid and air for driving the turbine.

These and other objects, features and advantages of the invention will, in part, be pointed out with particularity, and will, in part, become obvious from the following more detailed description of the invention taken in conjunction with the accompanying drawing which forms an integral part thereof.

Briefly, the invention describes a dental drill which includes a handpiece having a neck portion projecting from the handpiece. Integral with the end of the neck portion is a drill head which includes a housing comprising a lower surface. A tubular shaft longitudinally extends at least partially through the housing and is adapted to receive a burr which can be inserted therein. The burr therefore, can extend from the lower surface downwardly to be used in the drilling operation. A driving means is positioned in the head for rotating the tubular shaft to thereby rotate the burr. A fluid conveying tube axially extends through the neck and connects to conduits which are positioned proximal to the shaft. The conduits terminate in discharge outlets adjacent the lower surface of the housing. A passage also axially extends through the neck and terminates in part on the lower surface. The handpiece is adapted to connect the fluid conveying tube to a source of water whereby water is supplied from the conduits at an angle to strike the burr. The handpiece also connects the passage to a source of vacuum to aspirate fluid and air from the vicinity of the burr.

In an embodiment of the invention, the driving means includes an air operated turbine which is connected to the shaft. The passage includes a section which passes transversely across the turbine whereby fluid and air aspirated into the passage causes the turbine to rotate thereby operating the driving means.

It will be understood throughout the following description and claims that the term "burr" is used as a general term and includes all types of drill bits, polishing wheels, grinding wheels, etc., as may be inserted into a dental drill for various dental uses.

BRIEF DESCRIPTION OF THE DRAWING

In the drawing.

In the various figures of the drawing, like reference characters designate like parts.

DESCRIPTION OF THE PREFERRED EMBODIMENT

Figure 1:
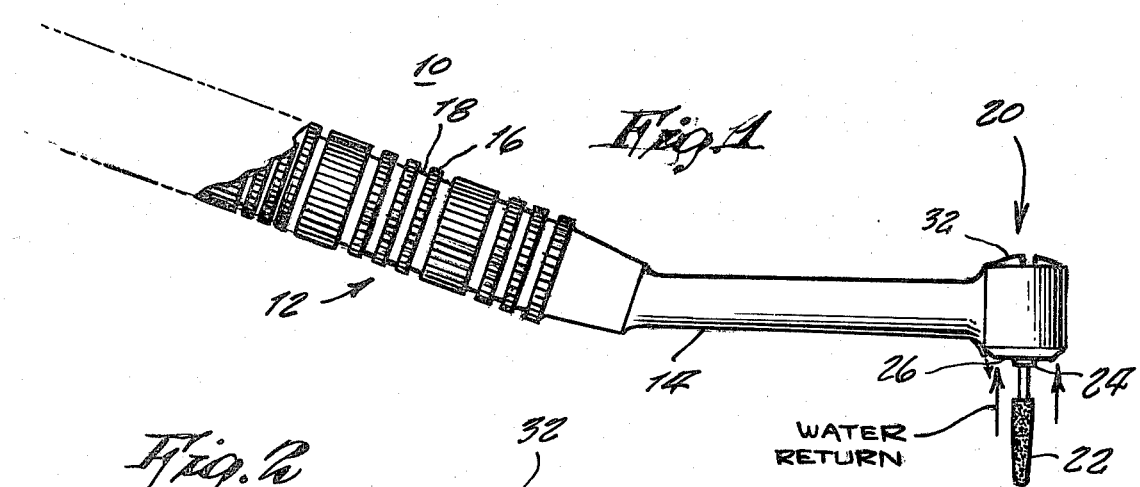
FIG. 1 is a side view of the lower end of a dental drill including the features of the present invention.
Figure 2:
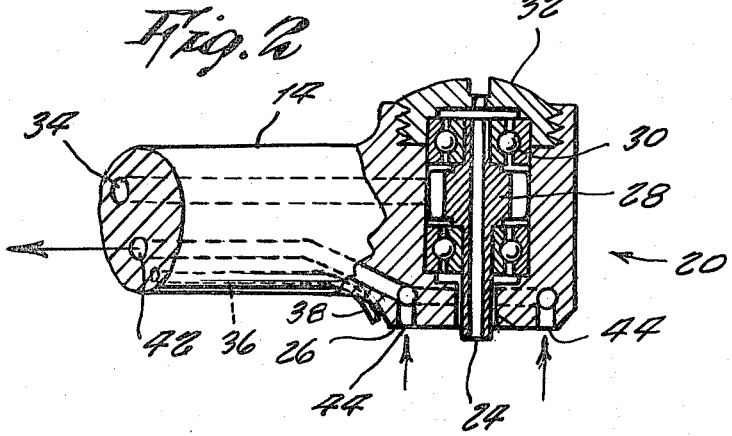
FIG. 2 is an enlarged partially sectioned view of the drill head and neck.

Referring now to FIG. 1 there is shown a portion of the drill 10 including a handpiece 12 having a neck 14 projecting from the handpiece. The handpiece 12 typically includes the usually knurled sections 16 permitting a better grip. At the end of the neck 14, and integral therewith, is the drill head shown generally at 20 in which a burr can be inserted. The burr is locked into a shaft 24 longitudinally extending within the drill head and slightly projecting from the lower surface 26 of the drill head. The drill head includes means to aspirate a fluid, generally water and air, from the vicinity of the drilling operation. The handpiece, neck, and head is typically of one piece. The only parts which are removable are the screw 32 which permits entry into the drill head for removal of the turbine.

The drill is shown to have the shaft 24 coupled to the turbine 28 which is driven to rotate within the head 20 on the ball bearings 30. The turbine is driven by means of air flowing into the passageway 34 which extends through the neck 14 and passes transversely across the turbine vanes. The handpiece interconnects the passageway 34 to a source of air pressure whereby, when energized, the air pressure passing through the passageway 34 will rotate to the turbine to thereby also rotate the shaft 24. A burr inserted within the shaft will thereby rotate concurrently therewith.

A fluid conveying tube 36 also passes through the neck 14 and exits at the conduits 38 which are positioned proximal to the drill head 20. The conduits 38 are placed at an angle toward the burr. The handpiece interconnects the fluid conveying tube 36 to a source of fluid, typically water, so that water can pass through the conduit 36. As the water exits from the conduits 38, it strikes the rotating burr and becomes a mist which can spray in all directions to thereby provide a spray of the area being drilled, to remove debris, contaminants, etc., and maintain the drilling area cool and clean.

Passageway 42 is also contained in the neck 14 and continues into the head 20 where it terminates in ports 44 on the lower surface 26 of the drill head 20. The handpiece interconnects the passage 42 to a source of vacuum so that when operated, fluid and air will be aspirated into the ports 44 to be removed from the area being drilled.

Figure 3:
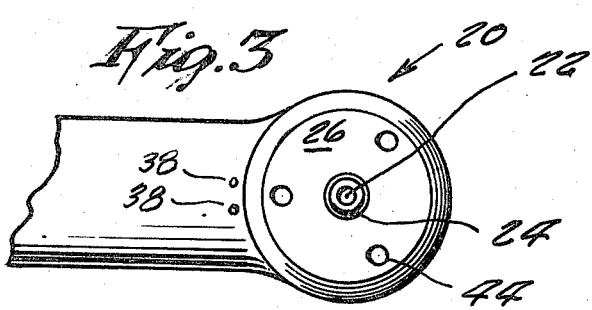
FIG. 3 is a bottom view of the drill head shown in FIG. 2.

As will be noted from FIG. 3, the discharge outlets 38 which provide water are placed in proximale relationship with the drill head 20, being placed at an angle with respect to the rotating burr so that the water can be discharged to strike the burr and thereby form into a mist. The aspirating ports 44 are shown equally spaced around the shaft 24. The aspirating ports 44 are spaced toward the outer part of the head so that they can aspirate over a wide range of coverage from the drill area.

Utilizing the foregoing described embodiment, as the dentist uses his drill, water will be sprayed onto the rotating burr which will disperse it into a mist spraying the drilling area. Air pressure will be provided to turn the turbine thereby driving the drill. Simultaneously therewith, water and air will be aspirated back into the drill head. In this manner, the water will have less of an opportunity to accumulate on the bottom of the patient's mouth since it will be aspirated back into the drill head before it can accumulate very much. Furthermore, since the aspiration occurs directly into the drill head, the spray will not have an opportunity to extend too far from the drilling area but will be maintained in the drill area thereby preventing it from being breathed by the dentist. Also, it will help prevent misting and fogging of the mirror and other instruments used by the dentist.

The high speed suction provided by the aspirator at the handpiece can eliminate the necessity of the extra hose being held by an assistant which can often collect the soft tissues and block the view of the dentist. The suction at the handpiece serves as sufficient aid to the low volume aspirator hanging in the patient's mouth to thereby remove the fluid without the need of the assistant. However, most important is that it prevents aspiration of the mist by the dentist, the assistant and the patient.

Additionally, by aspirating directly in the vicinity of the drilling area, the drilling area is maintained relatively free and clear. Simultaneous effect of the mist spray with the immediate suction thereof provides improved results in clearing the drill area from debris and contaminants and provides additional cooling of the teeth.

Figure 4:
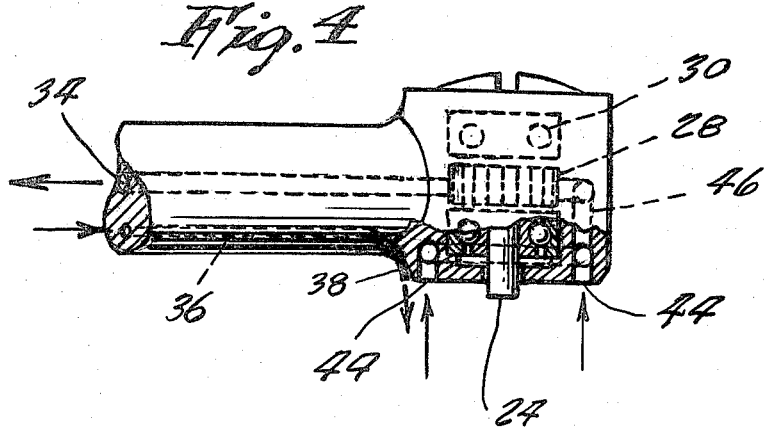
FIG. 4 is a side elevational view, partially sectioned of another embodiment of a drill head, in accordance with the present invention.

Referring now to FIG. 4, there is shown another embodiment of the present invention whereby the aspirated fluid and air can be utilized to aid in the driving of the turbine. In FIG. 4, again the water is provided by means of the fluid conveying passes 36 terminating in the discharge outlets from the conduit 38. However, it will be noted that there is not provided any air pressure passage for driving the turbine. Instead, the ports 44 interconnect with the passage 46 which passes transversely across the turbine 28 so that fluid and air aspirated into the ports 44 will pass across the turbine to turn it and thereby drive the shaft 24 which will in turn rotate the burr.

Utilizing the embodiment of FIG. 4, not only is there improved results as far as clearing the drilling area by removing the spray mist, but there is an improved efficiency be using such aspirators for fluid and air to actually drive the burr itself. In using the embodiment of FIG. 4, the noise occurring from the air pressure which conventionally drives the turbine and escapes at the drill head, is eliminated. As a result, the embodiment of FIG. 4 will be much quieter by eliminating the high pitched whine of the air escaping at the drill area. It will be understood that a combination of both air pressure externally provided through a passageway as well as the aspirated fluid and air could simultaneously be utilized to drive the turbine.

There has been disclosed heretofore the best embodiments of the invention presently contemplated. However, it is to be understood that various changes and modifications may be made thereto without departing from the spirit of the invention.

What is claimed is:

1. A dental drill comprising a handpiece having a neck portion, a drill head integral with the end of neck portion and including a housing having an integral lower surface formed of unitary construction with the housing, and a removable cap covering the upper end of the housing, a tubular shaft longitudinally extending at least partially through said housing and adapted to receive a burr inserted therein which can then extend through an opening in said lower surface, a turbine transversely positioned in said housing and coupled to said shaft for rotating said tubular shaft thereby rotating the burr, a water conveying tube axially extending through said neck and connecting to conduits positioned proximate to said shaft and terminating in discharge outlets adjacent the lower surface of said housing and angularly facing toward the extending shaft whereby the water supplied can strike a rotating burr to be dispersed into a mist, and a fixed passage axially extending through said neck and transversely crossing said turbine then downwardly extending toward the lower surface where it splits up into a number of longitudinal extending pipes each terminating in a discrete port formed through the lower surface with the ports being equally spaced about the shaft and positioned adjacent the outer edge of said lower surface, said handpiece adapted to connect the fluid conveying tube to a source of water, and to connect said passage to a source of vacuum to aspirate said water mist and air from the vicinity of the burr whereby the water and air aspirated through the discrete ports pass upward through the individual extending pipes and then join together into said fixed passage to transversely cross the turbine thereby operating the turbine.

2. A dental drill as in claim 1 and wherein said shaft includes ball bearing means on which said turbine can rotate within said housing.

* * * * *